US00PP25830P3

(12) United States Plant Patent
Bradford et al.

(10) Patent No.: US PP25,830 P3
(45) Date of Patent: Aug. 25, 2015

(54) PEACH TREE NAMED 'SIERRA PRINCESS'

(50) Latin Name: *Prunus persica*
Varietal Denomination: Sierra Princess

(71) Applicants: Lowell Glen Bradford, Le Grand, CA (US); Jon Michael Quisenberry, Merced, CA (US)

(72) Inventors: Lowell Glen Bradford, Le Grand, CA (US); Jon Michael Quisenberry, Merced, CA (US)

( * ) Notice: Subject to any disclaimer, the term of this patent is extended or adjusted under 35 U.S.C. 154(b) by 108 days.

(21) Appl. No.: 13/998,855

(22) Filed: Dec. 16, 2013

(65) Prior Publication Data

US 2015/0173277 P1 Jun. 18, 2015

(51) Int. Cl.
*A01H 5/08* (2006.01)

(52) U.S. Cl.
USPC ..... Plt./196

(58) Field of Classification Search
USPC ..... Plt./196
CPC ..... A01H 5/0868; A01H 5/0837
See application file for complete search history.

(56) References Cited

U.S. PATENT DOCUMENTS

PP7,066 P 12/1989 Bradford et al.
PP12,570 P2 4/2002 Bradford

*Primary Examiner* — Kent L Bell

(57) ABSTRACT

The present invention relates to a new and distinct variety of peach tree, *Prunus persica*, broadly characterized by a large size, vigorous, hardy, self-fertile, productive and regular bearing tree. The variety blooms during the mid to late blooming season and requires about 600 chilling hours. The fruit matures under the ecological conditions described in early August with the first picking on Aug. 2, 2013. The fruit is uniform, large in size, globose in shape, freestone in type, very firm in texture, white in flesh color, almost full red in skin color, and a tasty balance of light acid and sugar in flavor.

1 Drawing Sheet

Botanical classification: *Prunus persica.*
Variety denomination: 'Sierra Princess'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Sierra Princess'.

The present variety was hybridized by us in 2004 as a first generation cross using 'Diamond Princess' (U.S. Plant Pat. No. 7,066) peach as the selected seed parent and an unnamed white flesh peach (unpatented) as the selected pollen parent. The fruit of this cross was gathered that summer, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2008 we selected the present variety as a single tree from the group of seedlings described above. Subsequent to origination of the present variety of peach tree, we asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent 'Diamond Princess' peach (U.S. Plant Pat. No. 7,066) by having a vigorous tree with large blossoms, by being self-fertile, and producing freestone peaches that are mostly red in skin color, globose in shape, and firm in texture, but is quite distinguished therefrom by producing fruit that is white in flesh color instead of yellow, that is sweeter and less acidic in flavor, and that matures about thirty-five days later.

The present variety is most similar to 'Snow Princess' peach (U.S. Plant Pat. No. 12,570) by having a vigorous tree with large blossoms, by being self-fertile, and by producing white flesh freestone peaches that are large in size, mostly red in skin color, globose in shape, and firm in texture, but is distinguished therefrom by having globose instead of reniform leaf glands, by having a sweet instead of bitter tasting kernel, by blooming about 10 days later, and by producing fruit that has a balanced flavor between acid and sugar rather than subacidic, that can hang on the tree longer during the harvest season, and that matures about 10 days later.

SUMMARY OF VARIETY

In summary, the present peach variety is characterized by a large size, vigorous, hardy, self-fertile, productive and regular bearing tree. The variety blooms during the mid to late blooming season and requires about 600 chilling hours. The fruit matures under the ecological conditions described in early August with the first picking on Aug. 2, 2013. The fruit is uniform, large in size, globose in shape, freestone in type, very firm in texture, white in flesh color, almost full red in skin color, and a tasty balance of light acid and sugar in flavor.

DRAWING

The accompanying photograph consists of four whole fruits positioned to display the characteristics of the skin color and form, one divided fruit to reveal the flesh and stone, two insets to reveal buds and blossoms, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Aug. 10, 2013, on the original tree during its ninth growing season. The blossom and flower descriptions were made the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: 'Diamond Princess' (U.S. Plant Pat. No. 7,066) peach.

Pollen parent: Unpatented white flesh peach.

Tree

Size: Large, reaching and maintaining a height of 9' [2.74 m.] and a spread of 10' [3.05 m.] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 600 hours.

Trunk:

- *Size*.—Stocky, reaching a maximum diameter of 6¼" [159 mm.] after the ninth growing season.
- *Texture*.—Medium shaggy.
- *Bark color*.—A Light grayish brown [60. l.gy.Br] and Dark grayish brown [62. d.gy.Br] variegation with Light grayish yellowish brown [79. l.gy.yBr] crevices present.
- *Lenticels*.—Approximate Number Per Square Inch: 11. Color: Light yellowish brown [76. l.yBr]. Average Size: ⅛" [3.2 mm.]. Shape: Eye-shaped, elongated.

Branches:

- *Size*.—Diameter of main scaffold is 4" [102 mm.] measured 12" above the crotch, diameter of limb is 2½" [64 mm.] measured 12" above the first fork.
- *Texture*.—Smooth on first and second year wood, increasing roughness with age.
- *Color*.—1st Year Wood Topside: Grayish red [19. gy.R]. 1st Year Wood Underside: Brilliant yellow green [116. brill.YG]. Older Wood: A Light grayish brown [60. l.gy.Br] and Grayish brown [61. gy.Br] variegation with Light brown [57. l.Br] crevices present.
- *Lenticels*.—Number Per Square Inch: About 30 on second year. wood. Color: Light yellowish brown [76. l.yBr]. Size size: 1/64" [0.4 mm.] to 1/16" [1.6 mm.] on second year wood. Shape: Rectangular, elongated.

Leaves:

- *Size*.—Large. Average Length: 5¾" [146 mm.]. Average Width: 1 9/16" [40 mm.].
- *Arrangement*.—Alternate.
- *Thickness*.—Medium.
- *Form*.—Elliptical.
- *Apex*.—Acuminate.
- *Base*.—Rounded to slightly obtuse.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Vein color*.—Light yellow green [119. l.YG].
- *Petiole*.—Average Length: 7/16" [11.1 mm.]. Average Thickness: 1/16" [1.6 mm.]. Color: Brilliant yellow green [116. brill.YG].
- *Stipules*.—Number: Usually 2 per leaf, up to 6 per growing tip. Average Length: ¼" [6.4 mm.]. Color: Moderate yellow green [120. m.YG] becoming Moderate reddish brown [43. m.rBr] with maturity.
- *Glands*.—Number: 2 to 8 per leaf. Position: Alternately positioned on petiole and base of blade. Size: Small. Form: Globose appearing when young taking on a reniform shape with maturity. Color: Brilliant yellow green [116. brill.YG] acquiring a Deep reddish brown [41. deep rBr] center with age.
- *Leaf buds*.—Pointed, medium in size.

Flower buds:

- *Hardiness*.—Hardy, with respect to central California winters.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Moderate purplish pink [250. m.pPk].

Flowers: Perfect, complete, perigynous, usually a single pistil, about thirty stamens, five sepal and petal locations alternately positioned.

- *Type*.—Showy, large.
- *Average flower diameter*.—1¾" [44.5 mm.].
- *Number of petals*.—Usually five, extra petal fragments occur occasionally, double blossoms rarely observed.
- *Petal shape*.—Circular to oval.
- *Petal margin*.—Entire, somewhat wavy.
- *Average petal diameter*.—11/16" [17.5 mm.].
- *Average petal length*.—¾" [19.1 mm.].

*Petal apex*.—Rounded.
*Petal base*.—Rounded to somewhat truncate.
*Petal color*.—Light pink [4. l.Pk] toward the apex, Moderate pink [5. m.Pk] toward the base on both sides.
*Anther color*.—Moderate red [15. m.R] over a Light yellow [86. l.Y] center at bloom onset.
*Stigma color*.—Light greenish yellow [101. l.gY].
*Average pistil length*.—1 1/16" [17.5 mm.].
*Average stamen length*.—9/16" [14.3 mm.].
*Sepal color*.—Dark purplish red [259. d.pR] on the outer surface.
*Sepal length*.—1/4" [6.4 mm.].
*Sepal width*.—3/16" [4.8 mm.].
*Sepal apex*.—Rounded to elliptical to match the sepal length and width.
*Sepal margin*.—Fairly smooth.
*Fragrance*.—Moderate.
*Blooming period*.—Medium to late, three days before 'Diamond Princess' (U.S. Plant Pat. No. 7,066) peach.
*Onset of bloom*.—One percent on Mar. 9, 2013.
*Date of full bloom*.—Mar. 16, 2013.
*Duration of bloom*.—One to two weeks, dependent on ambient temperature.
*Number per cluster*.—1 to 3 with single flowers most common.

FRUIT

Maturity when described: Firm ripe, Aug. 10, 2013.
Date of first picking: Aug. 2, 2013.
Date of last picking: Aug. 16, 2013.
Size: Uniform, large.
*Average diameter axially*.—2 15/16" [74.6 mm.].
*Average diameter across suture plane*.—3 1/8" [79.4 mm.].
*Average diameter across cheek plane*.—3 1/8" [79.4 mm.].
*Typical weight*.—9.7 ounces [275 grams].
Form: Uniform, globose, mostly symmetrical.
*Longitudinal section form*.—Slightly oblate.
*Axial view*.—Round.
Suture: A distinct line with slight stitching located in a shallow groove that extends from the base, along the side, to just beyond the pistil point.
*Near the base*.—A shallow but sharp groove.
*Along the side*.—A shallow trough.
*Near the apex*.—A line located in a shallow groove.
Ventral surface: Rounded, almost no lipping except toward the apex.
Lips: Slightly unequal.
Cavity: Flaring, elongated in the suture plane, suture showing on both sides, Pale Yellow [89. p.Y] stem markings typical.
*Depth*.—5/8" [15.9 mm.].
*Breadth*.—1 3/8" [34.9 mm.].
Base: Truncate.
Apex: Rounded to slightly truncate.
Pistil point: Negligible in length, usually depressed within the suture.
Stem: Medium.
*Average length*.—3/8" [9.5 mm.].
*Average width*.—3/16" [4.8 mm.].
Skin:
*Thickness*.—Medium.
*Surface*.—Pubescent.
*Tenacity*.—Tenacious to flesh.
*Astringency*.—Non-astringent.
*Tendency to crack*.—None observed in dry season.
*Color*.—Very deep red [14. v.deep R] smoothly transitioned into a Deep pink [3. deep Pk] background.
*Down*.—Moderate, short, does not roll up when rubbed.
Flesh:
*Color*.—White [263. White] with Deep red [13. deep R] streaking toward stone.
*Surface of pit cavity*.—Covered with Deep red [13. deep R] to Deep pink [3. deep Pk] fibers.
*Amygdalin*.—Slight, but detectible.
*Juice*.—Moderate, rich.
*Texture*.—Crisp, melting, very firm with the ability to hang on the tree for two weeks during the harvest period.
*Fibers*.—Abundant, fine.
*Ripens*.—Fairly evenly.
*Flavor*.—Very slight acid balanced with strong sugar, typically 18 brix.
*Aroma*.—Very slight.
*Eating quality*.—Excellent.

STONE

Type: Freestone.
Form: Oval.
Hilum: Narrow.
Base: Rounded.
Apex: Acuminate.
Sides: Fairly equal.
Surface: Irregularly furrowed toward the apex, pitted toward the base.
Ridges: Jagged.
External color: Dark reddish brown [44. d.rBr].
Pit wall color when cracked: Strong brown [55. s.Br].
Cavity surface color: Strong yellowish brown [74. s.yBr].
Average pit wall thickness: 1/4" [6.4 mm.]
Average width: 1" [25.4 mm.].
Average length: 1 1/2" [38.1 mm.].
Average breadth: 7/8" [22.2 mm.].
Tendency to split: None observed.
Kernel:
*Form*.—Oval.
*Skin color*.—Strong brown [55. s.Br] when first removed.
*Pellicle color*.—Light grayish brown [60. l.gy.Br].
*Vein color*.—Grayish brown [61. gy.Br].
*Taste*.—Sweet.
*Viable*.—Yes.
*Average width*.—7/16" [11.1 mm.].
*Average length*.—3/4" [19.1 mm.].
*Amygdalin*.—Scant.

Use

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Snow Princess' peach (U.S. Plant Pat. No. 12,570) by having a vigorous tree with large blossoms, by being self-fertile, and by producing white flesh freestone peaches that are large in size, mostly red in skin color, globose in shape, and firm in texture, but is distinguished therefrom by having globose instead of reniform leaf glands, by having a sweet instead of bitter tasting kernel, by blooming about 10 days later, and by producing fruit that has a balanced flavor between acid and sugar rather than subacidic, that can hang on the tree longer during the harvest season, and that matures about 10 days later.

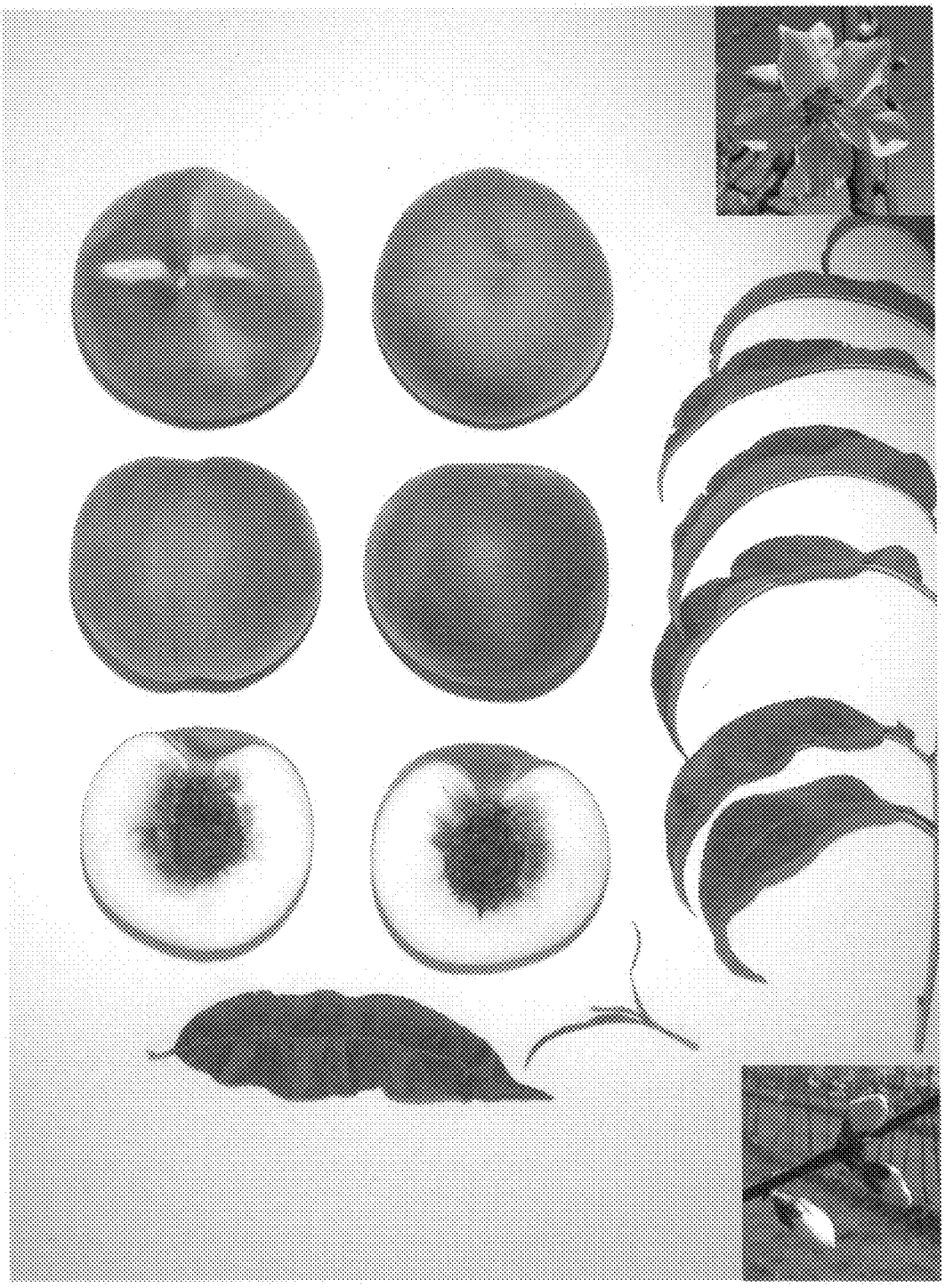

* * * * *